US007051748B2

(12) United States Patent
VanBasten

(10) Patent No.: US 7,051,748 B2
(45) Date of Patent: May 30, 2006

(54) ROLL-UP POOL FOR A DECONTAMINATION SYSTEM

(76) Inventor: Willem F. VanBasten, P.O. Box 696, Hatboro, PA (US) 19040

(*) Notice: Subject to any disclaimer, the term of this patent is extended or adjusted under 35 U.S.C. 154(b) by 263 days.

(21) Appl. No.: 10/785,712

(22) Filed: Feb. 24, 2004

(65) Prior Publication Data

US 2006/0070654 A1 Apr. 6, 2006

Related U.S. Application Data

(60) Provisional application No. 60/451,729, filed on Mar. 4, 2003.

(51) Int. Cl.
*A47K 3/062* (2006.01)
*A61M 1/00* (2006.01)

(52) U.S. Cl. ........................ 137/15.01; 137/312; 4/585

(58) Field of Classification Search ............. 137/15.01, 137/312; 4/585; 220/571
See application file for complete search history.

(56) References Cited

U.S. PATENT DOCUMENTS 4,890,343 A * 1/1990 Schlags ......................... 4/585
5,375,275 A * 12/1994 Sanders ......................... 4/599
6,088,848 A * 7/2000 Waterlyn ......................... 4/585
6,202,689 B1 * 3/2001 Williams .................... 137/312
6,568,419 B1 * 5/2003 Robinson et al. ........... 137/312
6,895,871 B1 * 5/2005 Smith et al. ................ 108/115

* cited by examiner

*Primary Examiner*—Kevin Lee
(74) *Attorney, Agent, or Firm*—William H. Eilberg

(57) ABSTRACT

A roll-up pool combines a collection basin and an elevation grid system into one unit that can be set up for use in seconds. The roll-up pool includes a bottom portion and wall portions, as well as an upper surface. A set of elevation pieces are located between the upper surface and the bottom portion, and are bonded to these components. All of these components are made of a material which is sufficiently flexible to allow the structure to be wound into a roll. When decontamination is required, the roll is unwound to provide a collection basin having an elevation grid system. In another embodiment, the rolled structure includes only the elevation grid system, and is intended for deployment in a collection basin that already exists. The invention substantially reduces the time and effort required to decontaminate victims of industrial accidents or chemical or biological attack.

18 Claims, 5 Drawing Sheets

4' BY 4' FOR
SINGLE SHOWER STALL

4' BY 10' FOR
TRIPLE SHOWER STALL

6' BY 12' FOR
12' NON-AMBULATORY

6' BY 18' FOR
18' NON-AMBULATORY

ROLL-UP POOL FOR A DECONTAMINATION SYSTEM

CROSS-REFERENCE TO PRIOR APPLICATION

Priority is claimed from U.S. provisional patent application Ser. No. 60/451,729, filed Mar. 4, 2003, the disclosure of which is incorporated by reference herein.

BACKGROUND OF THE INVENTION

The present invention relates to the field of decontamination systems, and provides a portable, rapidly installable pool for collecting run-off water used in a decontamination system.

The need for decontamination arises in many contexts. Personnel may become contaminated during industrial accidents, such as leaks in chemical plants, or by spillage of hazardous substances as a result of railroad or highway accidents. Leakage of radiation from a nuclear reactor can also cause contamination of personnel in the vicinity. More recently, the threat of chemical and biological attacks has highlighted the need for immediate decontamination of personnel that may come into contact with harmful substances such as bacteria, viruses, or chemical agents.

The most immediate and most simple step in the decontamination process is to wash away the contaminants with water, such as by showering. Therefore, one simple method of decontamination, practiced in the prior art, has been to provide a temporary shelter that includes a shower stall, or its equivalent, and a supply of water. These temporary shower stalls are provided with hot water heaters and temporary plumbing to create a shower that can remove most or all of the contaminant material from a person undergoing decontamination. After showering, the user may proceed to a separate drying stall, and the drying step may be followed by the step of inspecting the subject for signs of residual contaminants and applying more sophisticated decontamination treatments if necessary.

A major problem with the procedure described above is the containment of run-off water. Since the aim of the decontamination process described above is to wash away the contaminants as soon as possible, it is clear that the waste water from the shower system is likely to contain a large concentration of such contaminants. It is therefore not advisable for a user to stand directly in the contaminated water.

It is also important to contain the run-off water, and to dispose of it in a safe manner. If the temporary shower stall includes a shower curtain, and the unit is installed outside, water may escape the stall when the curtain is fluttering in windy conditions. Also, containment of water is made more difficult when the temporary shower stall is assembled on sloping terrain, because water tends to overflow from the low end of the stall.

In the prior art, it has been known to deal with the problem of handling run-off water by providing a catch basin having an elevated grid. Typically the grid is positioned at least about two inches above the ground level. The user walks on the grid, while the run-off water flows through the grid and is collected in the basin below. A pump transfers the water from the basin into a container suitable for holding the contaminated water. This arrangement minimizes the exposure of the user to the contaminants.

While the above-described solution ameliorates the problem of how to handle the contaminated run-off water, it has substantial disadvantages. Since a typical pool is ten feet long, it is usually necessary to provide several grid sections to span the entire floor area. Moreover, when the pool fills with water, the grid sections may begin to float, causing a hazard to the users. Most importantly, the grid requires time to assemble. When an industrial accident occurs, or when there is a chemical or biological attack, it may be necessary to set up a decontamination unit very quickly. The need to deploy grids as described above substantially slows the process of assembling the decontamination unit.

The present invention provides a pool structure that combines a basin and a plurality of grid sections into one unit, which can be wound up and stored as a roll for deployment at a moment's notice. Indeed, the pool of the present invention can be set up in minutes, or even seconds, providing a convenient and safe means for handling contaminated run-off water in an emergency situation.

SUMMARY OF THE INVENTION

The present invention comprises a roll-up pool which includes a bottom portion and a plurality of walls, the bottom portion and walls together defining a pool for containing liquid. A plurality of elevation pieces are bonded to the bottom portion of the pool. An upper surface, on which the user may walk, is bonded to the top of the elevation pieces. The bottom portion, the walls, and the upper surface are relatively stiff, but are still sufficiently flexible to allow the entire structure to be wound into a roll and later unwound.

The upper surface may be a generally solid material, such as a stiff fabric, or it can comprise a mesh. In either case, water can flow either along or through the upper surface, and can be collected at the bottom of the pool and pumped away for later disposal.

In another embodiment, the invention includes only an elevation grid system, suitable for providing elevation grids in a decontamination system that already includes a pool. The elements of the elevation grid system are the same as those of the roll-up pool, except that the grid system does not include the pool walls or the means for pumping water from the pool.

The invention may also include fasteners, or other means for connecting a shower curtain, used as part of a temporary shower stall, to the roll-up pool. In this way, the invention prevents water from the shower from exiting the shower stall when the device is used outside in windy conditions.

The roll-up pool of the present invention also includes at least two drain connections, preferably located at diametrically opposing positions, thereby assuring that there will always be a convenient drain connection when the pool is set down on sloping terrain, regardless of the orientation of the pool. This feature further enables the pool of the present invention to be deployed very rapidly.

The invention also includes a method of decontamination, which includes unwinding a rolled-up combined pool and grid structure, and placing the unwound structure under a shower head, wherein the pool and grid structure together comprise a collection basin. In another embodiment, the method includes unwinding a rolled-up grid structure, and placing the unwound structure in a collection basin.

The invention therefore has the primary object of providing a portable, compact, and rapidly deployable pool for decontamination systems.

The invention has the further object of providing a pool for decontamination, wherein the pool includes an elevation grid.

The invention has the further object of substantially reducing the time required to set up a pool in a decontamination system.

The invention has the further object of reducing the likelihood of recontamination by run-off water, in a water-based decontamination system.

The invention has the further object of providing a compact, easily stored, and rapidly deployable elevation grid system for use in a decontamination pool.

The invention has the further object of providing a compact, easily stored, and rapidly deployable roll-up pool, suitable for use in outdoor environments.

The invention has the further object of providing a compact, easily stored, and rapidly deployable roll-up pool, which can be rapidly set up on sloping terrain.

The invention has the further object of providing a method of rapidly setting up a decontamination pool for emergency or other use.

The reader skilled in the art will recognize other objects and advantages of the present invention, from a reading of the following brief description of the drawings, the detailed description of the invention, and the appended claims.

DETAILED DESCRIPTION OF THE INVENTION

Figure 1:
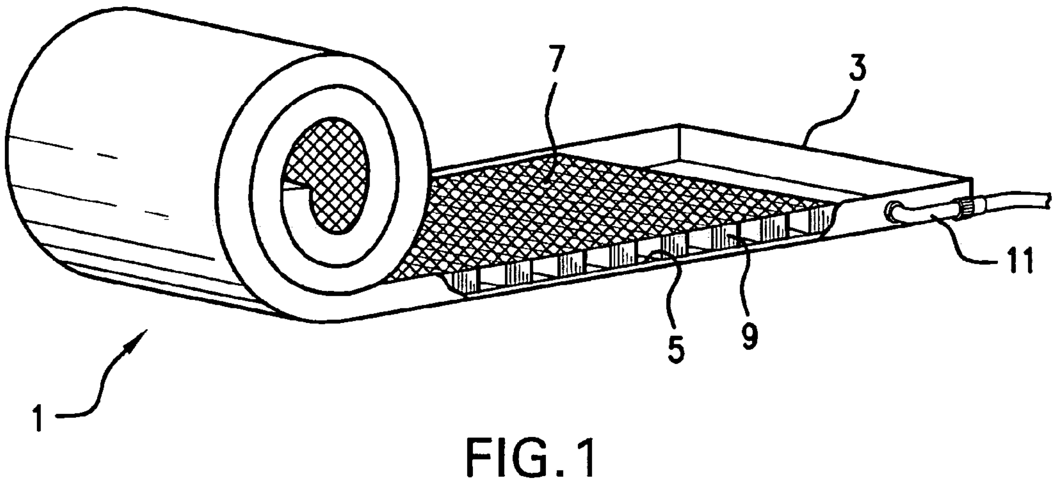
FIG. 1 provides a perspective view of the roll-up pool of the present invention.
Figure 3:
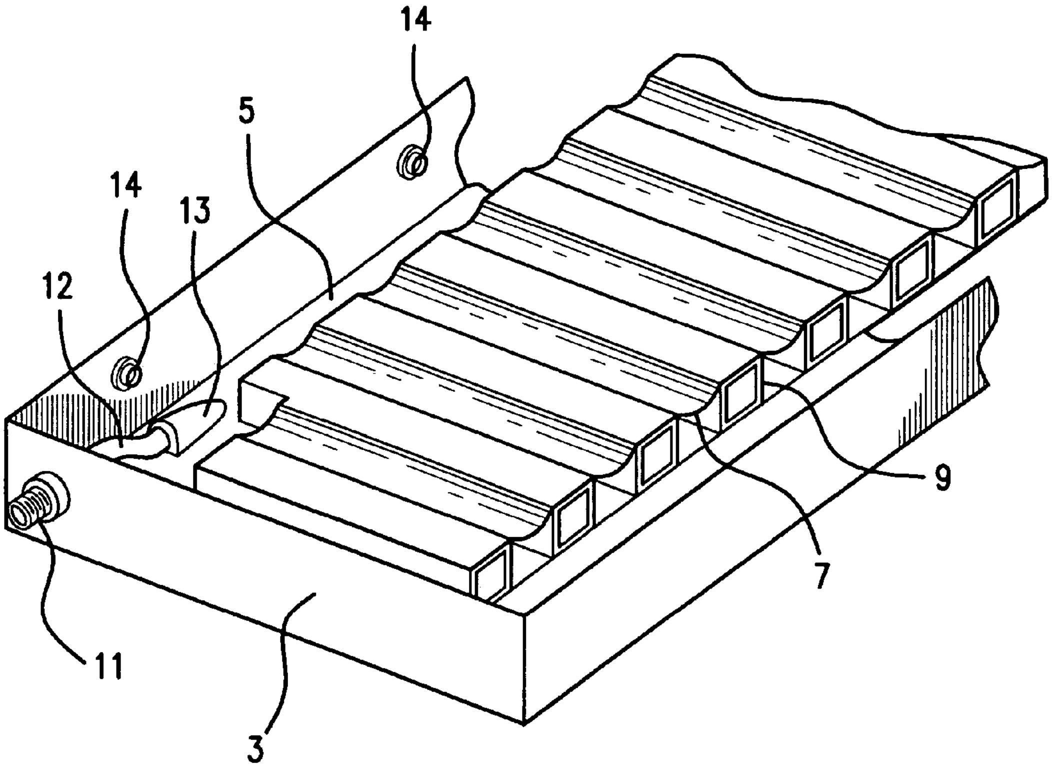
FIG. 3 provides a fragmentary and broken-away perspective view of a portion of the roll-up pool of the present invention.
Figure 4:
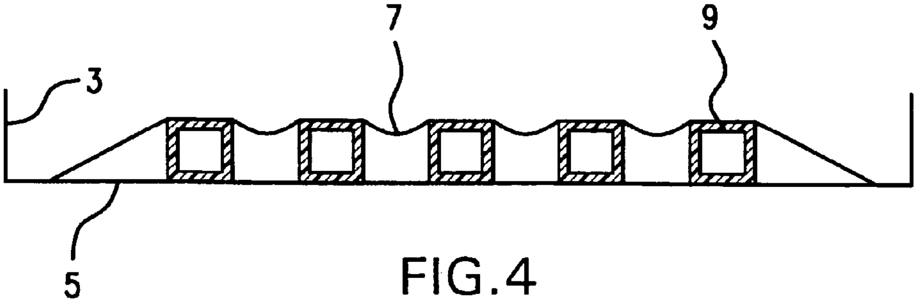
FIG. 4 provides a detail of a cross-section showing the elements of the grid of the present invention.

FIG. 1 provides a perspective view of a preferred embodiment of the present invention. FIGS. 3 and 4 provide additional details. FIG. 1 shows roll-up pool 1 in a partially rolled-up and partially unwound condition. The pool 1 is defined by bottom portion 5, preferably made of heavy-duty reinforced vinyl, or a stiff fabric, and by pool wall 3 which is also preferably made of the same material used to form the bottom portion, and which is welded to the bottom. The invention is not limited, however, by the specific choice of materials for the pool wall and floor, or by the means of assembly of the components. It is desirable that the pool wall and floor be sufficiently stiff and heavy that it can maintain its function of containing run-off water, but sufficiently flexible that it can be wound into a roll as shown in the figure.

The pool further includes an elevated grid or deck 7 which is supported by a plurality of elevation pieces 9. The deck 7 may be a solid piece of material, such as a stiff fabric, which defines channels that guide the run-off water to the sides of the pool, or it may be made of a mesh that inherently allows run-off water to flow through it. The deck is shown as a mesh in FIG. 1, and as a solid material in FIGS. 3 and 4. In either case, the deck is sufficiently strong to allow a user to walk on the deck. The mesh can be formed of nylon or vinyl, or other sturdy material that can be adhesively or otherwise bonded to the elevation pieces. The deck is preferably cemented or glued to the upper portions of the elevation pieces 9. The elevation pieces are, in turn, cemented or glued to the bottom portion 5 of the pool. It is preferred, but not absolutely required, that the elevation pieces be spaced apart by a distance that is slightly greater than the height of each elevation piece.

In a preferred embodiment, the elevation pieces may be hollow rods of polyvinyl chloride (PVC) having two-inch square cross-sections. But other materials may be used instead, and the invention is not limited to one construction. The invention is also not limited to a particular shape or cross-sectional dimension of the elevation pieces. For example, the cross-section could be rectangular. It is even possible to use solid rods instead of hollow rods.

A pre-formed water pick-up connection 11 is provided at the end of the pool, as best shown in FIG. 3, to facilitate the connection of a hose to conduct run-off water away from the pool. The connection 11 is preferably of a size that will work with a standard garden hose. A pump (not shown) can be employed to pump the run-off water out of the pool and into a suitable container (also not shown). The water pick-up connection is fluidly connected, through conduit 12, to water pick-up 13.

The water pick-up 13 is essentially a hollow structure having a relatively large opening at its bottom. The pick-up sits on the bottom of the pool. The large opening defined by the pick-up enables a relatively large amount of water to flow rapidly out of the pool. The pick-up is used instead of, say, a simple hose, because the pick-up provides a structure having a larger area, to accommodate a larger flow of water. Also, the pick-up preferably sits as low as possible on the floor of the pool, so as to enable the pump to draw out as much water as possible. Unless the pick-up sits on the bottom of the pool, the pump will not remove all of the water collected in the pool.

FIG. 3 also shows snaps 14. The snaps are used to connect a shower curtain (having complementary snaps) with the wall 3 of the pool. Instead of snaps, one could provide buckles, or other fastening devices. The reason for the snaps or buckles is that the pool may be used in conjunction with a shower curtain that is installed outside. In windy conditions, the shower curtain can be blown aside, allowing water from the shower to escape. Even when the shower is used in calm conditions, or indoors, attachment of the shower curtain to the pool wall tends to insure that water from the shower is directed into the pool and does not go outside the pool.

In one preferred embodiment, the snaps or buckles are arranged at intervals of approximately three feet, along the upper portion of the pool wall. This spacing is only exemplary, and should not be interpreted to limit the invention.

In the arrangement shown in FIGS. 3 and 4, the deck 7 is a solid piece, made of a relatively heavy fabric or vinyl. As is best illustrated in the cross-sectional view of FIG. 4, the deck comprises a solid cover that is welded or cemented to the top portions of each of the elevation pieces 9. This cover is shown to sag somewhat, forming valleys between adjacent elevation pieces, so as to define drain channels for run-off water. The amount of sag is somewhat exaggerated in the figure, for purposes of illustration. The water flows in the valleys, generally parallel to the longitudinal axes of the elevation pieces. There is a clearance between the elevation pieces and the pool walls, so that water flowing along the channels will eventually reach the bottom of the pool, and will be pumped out as intended. In a typical decontamination environment, water is provided at a rate of only about two gallons per minute. Water flowing at this rate can be easily removed from the pool using the described structure.

Although the invention contemplates that deck 7 may be formed by a solid fabric (or other unbroken material), the preferred arrangement is the use of a mesh, as is specifically illustrated in FIG. 1. The mesh provides for more immediate drainage of water, which falls through the openings in the mesh, and also provides a more skid-resistant surface for personnel using the decontamination facility, as they walk along said surface.

Figure 5:
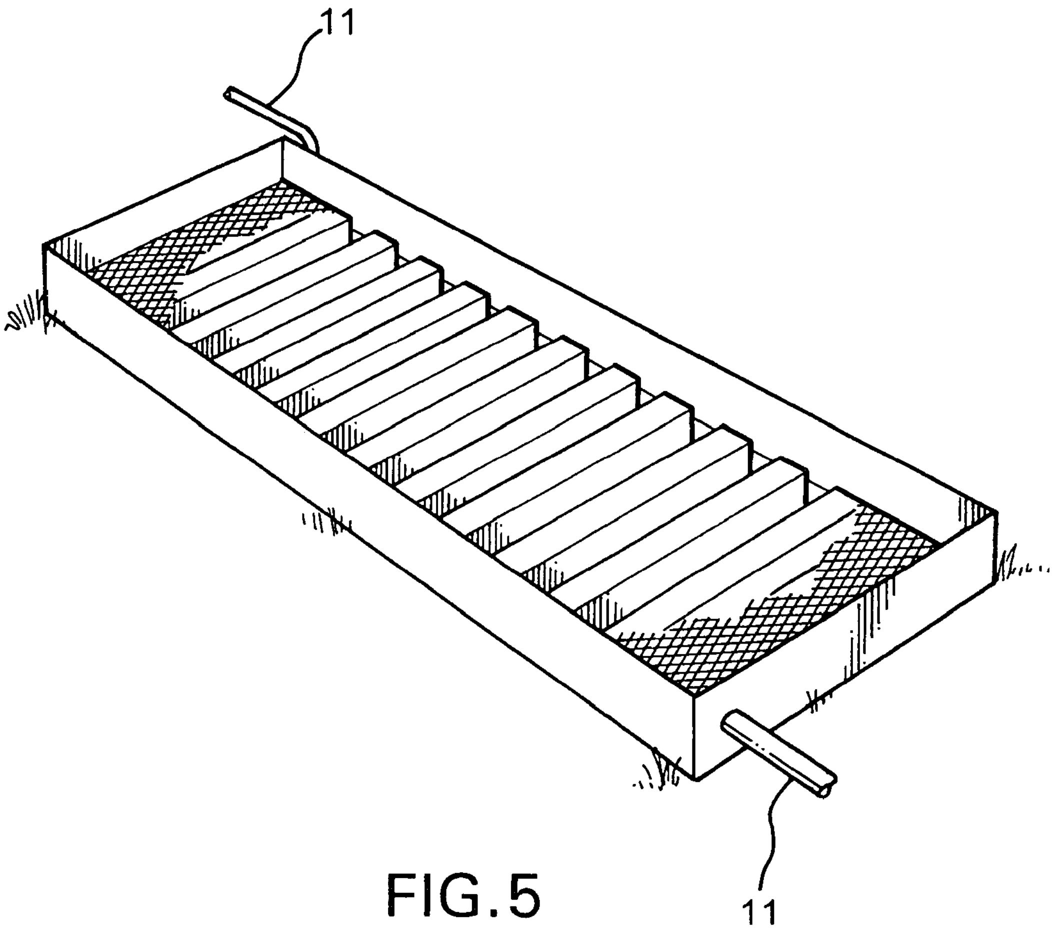
FIG. 5 provides a perspective showing the roll-up pool of the present invention, after it has been laid on the ground.

FIG. 5 provides a perspective view of a roll-up pool, made according to the present invention, in its fully extended condition. The figure shows the pool after it has been laid out on the ground. This figure also illustrates another feature of the invention, namely the provision of two water pick-up connections 11, located at opposite ends of the pool. The connections 11 are associated, respectively, with water pick-ups such as element 13 of FIG. 3, though the water pick-ups are not visible in FIG. 5.

The use of two water pick-up connections is important for the following reason. When the pool is installed outside, it may be installed on sloping terrain. For proper drainage, it is necessary for the water pick-up to be located at the low end of the pool. By providing water pick-up connections at both ends, it is possible to deploy the pool in any configuration. The installer will then connect the drain pump at the lower end. Thus, it is not necessary to take care, before setting the pool on the ground, to be sure that the pool will be oriented in a particular way. This arrangement therefore facilitates more rapid deployment of the pool.

Figure 6A:
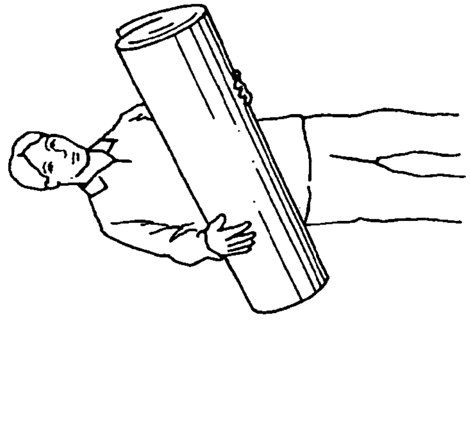
FIGS. 6*a*–6*d* provide perspective views showing the steps performed in setting up the roll-up pool of the present invention.
Figure 6B:
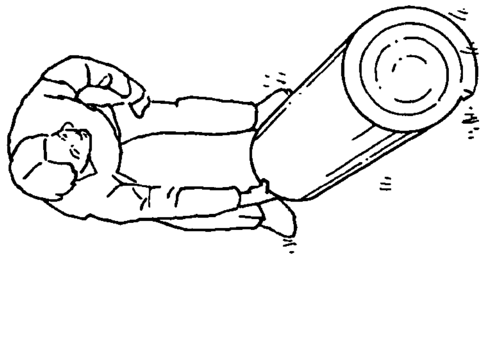
Figure 6C:
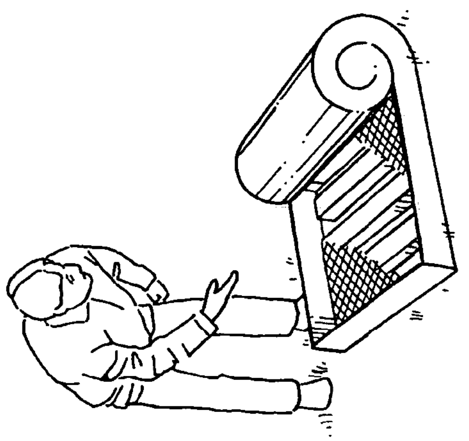
Figure 6D:
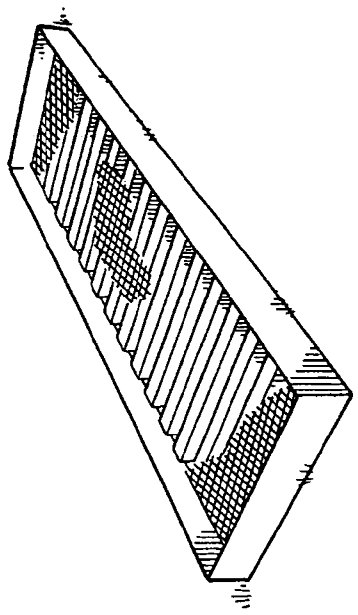

FIGS. 6*a*–6*d* provide perspective views showing the steps in the set-up of the roll-up pool. In FIG. 6*a*, the pool is retrieved from storage, the pool still being entirely wound into a roll. In FIG. 6*b*, the roll has been set down on the ground and is about to be unwound. In FIG. 6*c*, the pool is partially unwound, and in FIG. 6*d*, the pool has been completely unwound. For clarity of illustration, the figures do not show a shower apparatus disposed above the pool. The shower itself forms no part of the present invention.

Figure 7A:
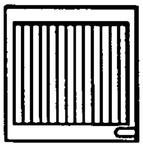
FIGS. 7*a*–7*d* provide diagrams, representing top views, showing alternative configurations of the roll-up pool of the present invention.
Figure 7B:
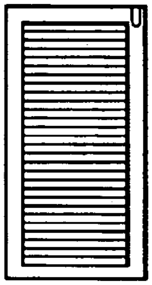

FIGS. 7*a* through 7*d* show various alternative contexts in which the present invention can be used. These figures are symbolic top views, showing the extent of the roll-up pool in relation to the shower stall used for decontamination. In FIG. 7*a*, a single roll-up pool occupies substantially the entire floor area of a single shower stall. Typical dimensions of the stall are 4×4 feet, but the invention should not be deemed limited by the particular dimensions in any given installation. In FIG. 7*b*, a triple shower stall, intended to accommodate three persons at once, is spanned by a single roll-up pool having dimensions of 4×10 feet.

Figure 7C:
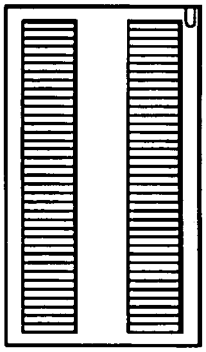
Figure 7D:
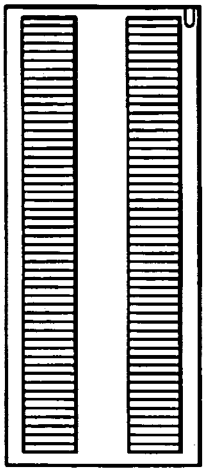

FIGS. 7*c* and 7*d* pertain to shower stalls used for non-ambulatory patients who require decontamination. Decontamination of non-ambulatory patients is typically performed with a larger collection pool having two elevated walkways which flank a central area. The elevated walkways are typically spaced about 24 inches apart. A gurney, or stretcher, or wheeled table carrying the person to be decontaminated, is wheeled or otherwise moved into the central area. Decontamination personnel can thus stand on either side of the patient, applying water in the decontamination process. The run-off water is collected in the basin below.

In the present invention, as applied to the case of a non-ambulatory patient, the elevated walkways are formed by the roll-up pool of the present invention, having the configurations indicated in FIGS. 7*c* and 7*d*.

Whether used for ambulatory or non-ambulatory persons, the pool works in essentially the same way, in that it provides a combined collection basin for contaminated run-off water, and a raised surface or platform on which decontamination personnel can stand.

Figure 2:
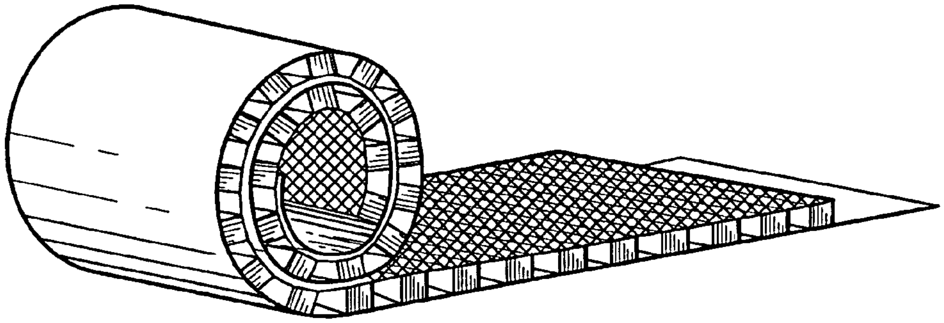
FIG. 2 provides a perspective view of an alternative embodiment of the invention which includes only an elevation grid system, formed as a roll-up structure.

FIG. 2 shows an alternative embodiment which provides an elevation grid only, and not a complete pool. The embodiment of FIG. 2 is similar to that of FIG. 1, in that it provides an elevation grid formed of a plurality of elevation pieces sandwiched between, and bonded to, a base portion and an upper surface which may be a mesh, as shown, or a solid piece. But, unlike the embodiment of FIG. 1, this embodiment does not include pool walls. The embodiment of FIG. 2 is intended for use in an environment where a pool already exists, and where all that is necessary is the installation of a grid. The embodiment of FIG. 2 allows the grid to be set up in seconds, simply by unwinding the grid and positioning it on the bottom of the pool. Except as described herein, the embodiment of FIG. 2 is otherwise similar in construction to that of FIG. 1.

The present invention is therefore especially suited for emergency use when it is necessary to decontaminate personnel who have been exposed to harmful substances. The pool of the present invention can be unwound and set up in minutes or seconds. The invention eliminates the need for the separate elevation grids that have been used in the prior art to keep persons being decontaminated away from contaminated run-off water. The present invention enables both a pool and its elevation grids to be set up in seconds.

The materials used to make the roll-up pool are preferably chosen such that they are chemically resistant to bleach and to other decontamination solutions.

When the decontamination process is completed, the pool can be again wound into a roll, and stored for the next use. The wound structure of the roll-up pool inherently minimizes the storage space required.

The roll-up pool of the present invention, by providing elevation pieces that are bonded to the pool structure, eliminates the problem associated with floating elevation grid sections. The present invention also inherently provides a non-skid surface, especially where the deck comprises a mesh. But even in the case where the deck is a solid fabric, the presence of the elevation pieces under the fabric tends to reduce the likelihood of skidding.

The invention can be modified in various ways. The size of the roll-up pool can be varied to accommodate different shower installations. The manner of attachment of the elevation pieces to the pool structure and/or to the deck can be changed. These and other modifications, which will be apparent to those skilled in the art, should be deemed within the scope of the following claims.

What is claimed is:

1. A roll-up pool for a decontamination system, comprising:

a) a bottom portion and a plurality of walls, the bottom portion and walls together defining a pool for containing liquid, b) a plurality of elevation pieces, the elevation pieces having top and bottom surfaces, the bottom surfaces of the elevation pieces being bonded to the bottom portion, and c) an upper surface which is bonded to the top surface of the elevation pieces, wherein the bottom portion, the walls, and the upper surface, are sufficiently flexible such that the pool can be wound and unwound.

2. The roll-up pool of claim 1, wherein the upper surface is a generally solid surface.

3. The roll-up pool of claim 1, wherein the upper surface comprises a mesh surface.

4. The roll-up pool of claim 1, further comprising means for removing water that has accumulated in the pool.

5. The roll-up pool of claim 4, wherein there are at least two water removing means, disposed at different locations on the pool.

6. The roll-up pool of claim 1, wherein the walls of the pool include fastening means attached to said walls.

7. The roll-up pool of claim 1, wherein the elevation pieces comprise hollow members having a generally rectangular cross-section.

8. A roll-up pool for a decontamination system, comprising a basin having a bottom portion and walls attached to the bottom portion, and a grid system affixed to the bottom portion such that the basin and the grid system comprise a one-piece structure, the bottom portion and walls being sufficiently flexible to allow the roll-up pool to be wound into a roll for storage.

9. The roll-up pool of claim 8, further comprising means for removing water that has accumulated in the pool.

10. The roll-up pool of claim 9, wherein there are at least two water removing means, disposed at different locations on the pool.

11. The roll-up pool of claim 8, wherein the walls of the pool include fastening means attached to said walls.

12. A roll-up pool for a decontamination system, comprising a bottom portion, a plurality of elevation pieces affixed to the bottom portion, the elevation pieces together defining a top-surface, and a grid affixed to said top surface, wherein the bottom portion and grid are sufficiently flexible to allow the roll-up pool to be wound into a roll for storage.

13. A portable elevation grid system for a decontamination pool, comprising:

a) a bottom portion, b) a plurality of elevation pieces, the elevation pieces having top and bottom surfaces, the bottom surfaces of the elevation pieces being bonded to the bottom portion, and c) an upper surface which is bonded to the top surface of the elevation pieces, wherein the bottom portion and the upper surface, are sufficiently flexible such that they can together be wound and unwound.

14. The roll-up pool of claim 13, further comprising means for removing water that has accumulated in the pool.

15. The roll-up pool of claim 14, wherein there are at least two water removing means, disposed at different locations on the pool.

16. In a method of decontaminating a patient, wherein the method comprises showering water on the person to be decontaminated, the showering being performed over a collection basin capable of collecting run-off water from the showering, the improvement wherein the showering is preceded by the step of unwinding a rolled structure, the rolled structure comprising a bottom surface, a top surface, a plurality of walls, and a plurality of elevation pieces disposed between, and bonded to, the bottom surface and the top surface, such that the unwound rolled structure comprises a collection basin for use in said showering.

17. The improvement of claim 16, wherein the rolled structure includes at least two water removal means, and wherein the method includes choosing one of said water removal means to be used for removal of water from the basin.

18. In a method of decontaminating a patient, wherein the method comprises showering water on the person to be decontaminated, the showering being performed over a collection basin capable of collecting run-off water from the showering, the improvement wherein the showering is preceded by the step of unwinding a rolled structure, the rolled structure comprising a bottom surface, a top surface, and a plurality of elevation pieces disposed between, and bonded to, the bottom surface and the top surface, and placing the unwound rolled structure in the collection basin.

* * * * *